United States Patent
Lo et al.

(10) Patent No.: US 9,173,899 B2
(45) Date of Patent: Nov. 3, 2015

(54) METHOD OF PREVENTING AND TREATING AUTISTIC SPECTRUM DISORDER

(71) Applicant: D & Y Laboratories Inc., Holden, MO (US)

(72) Inventors: Shui Yin Lo, Pasadena, CA (US); David L. Gann, Holden, MO (US)

(73) Assignee: D & Y Laboratories Inc., Holden, MO (US)

( * ) Notice: Subject to any disclaimer, the term of this patent is extended or adjusted under 35 U.S.C. 154(b) by 298 days.

(21) Appl. No.: 13/755,505

(22) Filed: Jan. 31, 2013

(65) Prior Publication Data

US 2014/0213667 A1    Jul. 31, 2014

Related U.S. Application Data

(60) Provisional application No. 61/615,543, filed on Mar. 26, 2012, provisional application No. 61/616,657, filed on Mar. 28, 2012.

(51) Int. Cl.
*A61K 33/00*    (2006.01)
*A61K 41/00*    (2006.01)
*A61K 47/46*    (2006.01)
*A61K 9/00*    (2006.01)
*A23L 1/29*    (2006.01)

(52) U.S. Cl.
CPC ............... *A61K 33/00* (2013.01); *A23L 1/296* (2013.01); *A61K 9/0053* (2013.01); *A61K 41/0004* (2013.01); *A61K 47/46* (2013.01)

(58) Field of Classification Search
CPC ....................................................... A61K 33/00
USPC ........................................................ 424/600
See application file for complete search history.

(56) References Cited

U.S. PATENT DOCUMENTS

| | | | |
|---|---|---|---|
| 2012/0207850 A1* | 8/2012 | Martin | 424/600 |
| 2013/0108723 A1* | 5/2013 | Martin | 424/769 |
| 2014/0242185 A1* | 8/2014 | Lo et al. | 424/600 |

* cited by examiner

*Primary Examiner* — Raymond Henley, III
(74) *Attorney, Agent, or Firm* — Henry M. Feiereisen LLC.

(57) ABSTRACT

Method of treating autistic spectrum disorder includes administration to a person of a product, which contains stable water clusters, such as stable double helix water clusters, by taking the products by mouth, applying the products on a skin of the person, intaking the product by breathing, introducing the products intravenously, etc.

13 Claims, No Drawings

METHOD OF PREVENTING AND TREATING AUTISTIC SPECTRUM DISORDER

CROSS-REFERENCE TO RELATED APPLICATIONS

This patent application claims its priority from non-provisional patent application Ser. No. 12/592,873 filed on Dec. 3, 2009, now U.S. Pat. No. 8,193,873, whose corresponding subject matter is incorporated here by reference thereto and which provides the basis for the claim to priority under 35 USC 119 (a)-(e).

This patent application also claims its priority from provisional patent application Ser. No. 61/615,543 filed on Mar. 26, 2012 and from provisional patent application Ser. No. 61/616,657 filed on Mar. 28, 2012 whose corresponding subject matter is incorporated here by reference thereto and which provide the basis for the claim to priority under 35 USC 119 (a)-(e).

BACKGROUND OF THE INVENTION

The present invention relates to a method of preventing and treating autistic spectrum disorder.

The number of children that suffer from autistic spectrum disorder is increasing at an alarming rate. However, there is no known cure for it. While the definition of the autistic spectrum disorder implies that it is linked to neurological problems, it was determined that most of the children with autistic spectrum disorder have other problems, such as gastrointestinal problems, and therefore treatment of autistic spectrum disorder as a problem of the brain is too limited. It is therefore believed that it is advisable to develop efficient methods of prevention and treatment of autistic spectrum disorder.

SUMMARY OF THE INVENTION

Accordingly, it is an object of the present invention to provide a new and efficient method of preventing and treatment of autistic spectrum disorder.

It is also an object of the present invention to provide a new method of detection of autistic spectrum disorder, which will allow targeted prevention and treatment of autistic spectrum disorder, based on its early and accurate detection.

In keeping with these objects and with others which will become apparent hereinafter, one feature of the present invention resides, briefly stated, in a method of preventing and treating autistic spectrum disorder of a person, in accordance with which a product which contains stable water clusters is administered to the person.

The administration of the product which contains the stable water clusters can prevent and treat the autistic spectrum disorder, as will be explained in detail herein below.

In accordance with the preferable embodiment of the present invention, the administration to the person of the product with the stable water clusters includes administering to the person the product which contains the stable water clusters that are double helix water clusters. The use of the products with the double helix stable water clusters provides high efficiency in prevention and treatment of the autistic spectrum disorder.

Various procedures can be used for administration of the products with stable water clusters to the person for prevention and treatment of autistic spectrum disorder.

The products with stable water clusters can be administered to the persons by taking the products with stable water clusters via his or her mouth for prevention and treatment of autistic spectrum disorder. The products with stable water clusters can be inhaled by the persons for prevention and treatment of autistic spectrum disorder. The products with the stable water clusters can be applied topically on a skin of the person to prevent or treat autistic spectrum disorder. The products with the stable water clusters can be introduced into the body of the person intravenous for prevention and treatment of autistic spectrum disorder. Also, combinations of the above specified procedures of administration can be used as well.

In accordance with the present invention the prevention of development of autistic spectrum disorder can be carried out at a very early stage, when a person is a child. In accordance with one approach a mother can drink a product with stable water clusters, which will be passed to a baby through breast feeding. If however the baby is fed with artificial milk, then the product with stable water clusters can be added to the artificial milk.

In accordance with the present invention, the products with the stable water clusters are applied on the body of a person on acupoints, which lie on meridians of a meridian system of the person. In particular the products with the stable water clusters can be applied on the acupoints which are located in hot spots or hot areas of the body. The hot spots or hot areas are characterized by temperatures which are higher than temperatures of adjoining areas of the body and are indicative of health problems in the organs of the person's body, associated with the autistic spectrum disorder.

In accordance with the present invention, the determination of the hot spots and hot areas on the body of the person can be carried out with the use of an infrared imaging system that takes thermal images of the person.

It is considered to be important to determine the hot spots or hot areas in twelve areas on the body of the person, such as front areas of left and right ears, inner points of left and right eyes, left and right near neck shoulder areas, left and right forehead temple areas, left and right collarbone areas, and left and right armpits areas. The products with the stable water clusters can be applied on acupoints associated with the hot spots in these areas.

The new features of the present invention are set forth in particular in the appended claims.

The invention itself, however, both as to its methods and products utilized, will be best understood from the following full description of preferred embodiments of the inventive method of preventing and treating autistic spectrum disorder.

DESCRIPTION OF THE PREFERRED EMBODIMENTS

In accordance with the present invention, a new method of preventing and treatment of autistic spectrum disorder. In accordance with the inventive method, a product which contains stable water clusters is administered to a person to prevent or to treat autistic spectrum disorder. In particular, the product with the stable water clusters can be administered, in which the stable water clusters are stable double helix water clusters.

The stable water clusters, water with stable water clusters, and products with stable water clusters, including double helix water clusters, in the present invention can be produced in accordance with methods disclosed in our patent application Ser. No. 12/592,873 filed on Dec. 3, 2009, which matured in U.S. Pat. No. 8,193,251 issued on Jun. 5, 2012. The stable water clusters, the water with stable water dusters, and products with stable water clusters, including double helix water clusters, are disclosed In our patent application Ser. No. 12/592,877 filed on Dec. 3, 2009.

In the method in accordance with the present invention, in order to prevent or treat autistic spectrum disorder, the stable water clusters, in particular the stable double helix water clusters, and the products with the stable water clusters can be administered to a person by taking via his or her mouth. A person can drink water or another liquid product with the stable water clusters, take pills or gels with the stable water clusters, etc., and thereby the stable water clusters reach digestive system of the person. A part of it, or sometimes the whole product if kept longer in the mouth, can be absorbed m the mouth and delivered to the blood stream directly.

The stable water clusters and the products with the stable water clusters can be also administered to the person by applying topically on the skin of the person. For example, a cream which contains the stable water clusters can be applied on and rubbed into the skin, and the stable water clusters will penetrate through the skin of the person's body.

The stable water dusters and the products with the stable water clusters can be administered to the person through breathing, by inhaling them. Nebulizers, inhalers and other devices, which are known per se in the art, can be utilized for this procedure of the product administration. In this case the stable water clusters are delivered upwards to the brain and downwards to the lungs of the person, without going through the digestive system.

The stable water clusters and the products with the stable water clusters can be introduced into the body of the person via an intravenous procedure. In this case the stable water clusters are delivered directly into the blood stream of the person.

It is also contemplated that various combinations of the above specified procedures can be used as well, to augment the prevention or treatment effect, to make the person more comfortable in the process of administration of the product with the stable water clusters for prevention or treatment of autistic spectrum disorder.

To improve the percentage and the rate of recovery sometimes it is essential to include other therapies, such as behavioral therapy, physiological therapy, acupuncture, herbs, drugs, biofeedback, massages, external qi applications and/or other alternative methods that are suitable for each individual person.

Prevention of development of autistic spectrum disorder can start from early childhood. This can be carried out in a way that a mother, as soon as a baby is born, consumes products with the stable water clusters, for example drinks water with the stable water clusters so that the stable water clusters are passed to the baby with the breast feeding. On the other hand, if a baby is fed with artificial milk, the a concentrate of the stable water dusters can be added to the artificial milk, which is directly given to the baby. Also, a cream with the stable water clusters can be applied on the skin of the baby. Since the stable water clusters are pure water, they have no harmful effect to babies, as do some vaccines.

In accordance with a further embodiment of the present invention, the products with the stable water clusters are applied to acupoints on the body of the person. The acupoint lies on meridians of a meridian system of a person and are associated with corresponding organs. It is important to apply the products with the stable water clusters on such acupoints which are located in so-called hot spots or areas that are indicative of corresponding health problems or inflammations of internal organs, since internal organs emit hot infrared radiation. The hot spots or areas have a temperature which is higher than the temperature of the areas that adjoin them.

The hot spots or areas can be determined by an infrared imaging system that take thermal images of the corresponding parts of the body of a person and detect the infrared radiation of the internal organs. The thermal images clearly show the hot spots or areas with the elevated temperatures.

There are twelve regions in which hot spots or areas should be considered. These areas are: front areas of left and right ears, inner points of left and right eyes, left and right near neck shoulder areas, left and right forehead temple areas, left and right collarbone areas, left and right armpits areas. The meridians of the meridian system of a person, which correspond to different internal organs extend through the above identified different areas. The difference in the temperatures of the left side and the right side of the corresponding area are also indicative of health problems of certain internal organs.

The applications of the products with the stable water clusters are performed on the acupoints which are located in the thusly determined hot spots or hot areas.

The application of the products on the acupoints corresponding to internal organs is based on our finding that autistic spectrum disorder is linked to health problems of certain internal organs, and therefore the application of the products with the stable water clusters is carried out on the acupoints associated with stomach meridian, bladder meridian, gallbladder meridian, large intestine meridian, small intestine meridian, etc.

The infrared imaging system can also be used to monitor the process of recovery by making thermal images of corresponding areas periodically during the process of treatment of a person by the administration of products with the stable water clusters. The thermal images taken later in this process are compared with the thermal images taken earlier in this process, to determine the changing temperatures in the corresponding areas and thereby the progress achieved as a result of the treatment in accordance with the inventive method.

The present invention is not limited to the details shown since various modifications and structural changes are possible without departing from the spirit of the invention.

What is desired to be protected by Letters Patent is set forth in particular in the appended claims.

The invention claimed is:

1. A method of treating autistic spectrum disorder of a person, comprising the steps of administering a product which contains stable water clusters to the person.

2. A method of treating autistic spectrum disorder as defined in claim 1, wherein said administering includes administering to the person the product which contains stable water clusters that are double helix water clusters.

3. A method of treating autistic spectrum disorder as defined in claim 1, wherein said administering includes taking by the person the product which contains the stable water clusters via his or her mouth.

4. A method of treating autistic spectrum disorder as defined in claim 1, wherein said administering includes inhaling the product which contain the stable water clusters by the person.

5. A method of treating autistic spectrum disorder as defined in claim 1, wherein said administering includes applying the product which contains the stable water clusters topically on a skin of the person.

6. A method of treating autistic spectrum disorder as defined in claim 1, wherein said administering includes introducing the product which contains the stable water clusters intravenously into a blood stream of the person.

7. A method of treating autistic spectrum disorder as defined in claim 1, wherein said administering includes administering selected from the group consisting of taking the product which contains the stable water clusters by the person via his or her mouth, inhaling the product which contains the stable water clusters by the person, applying the product which contains the stable water clusters topically on a skin of the person, introducing the product which contains the stable water clusters into a blood stream of the person, and combinations thereof.

8. A method of treating autistic spectrum disorder as defined in claim 1, wherein said administering includes delivering the product with the stable water clusters to a mother breast feeding the person who is a baby, so as to pass the product to the baby via breast feeding.

9. A method of treating autistic spectrum disorder as defined in claim 1, wherein said administering includes adding the product with the stable water clusters to an artificial milk to feed the person who is a baby.

10. A method of treating autistic spectrum disorder as defined in claim 1, wherein said administering includes applying the product with the stable water clusters on acupoints on a body of the person.

11. A method of treating autism spectrum disorder as defined in claim 1, further comprising determining on the body of the person spots which are associated with the acupoints and which are hot in that they have a surface temperature that is higher than a surface temperature of an adjoining surface area, and wherein said applying includes applying the product with the stable water clusters on the acupoints associated with the thusly determined hot spots on the body of the person.

12. A method of treating autism spectrum disorder as defined in claim 11, wherein said determining the hot spots on the body of the person includes using an infrared imaging system that takes thermal images of the person.

13. A method of treating autism spectrum disorder as defined in claim 11, wherein said determining of hot spots on the body of the person includes investigating substantially of twelve areas on the body of the person, containing front areas of left and right ears, inner points of left and right eyes, left and right near neck shoulder areas, left and right forehead temple areas, left and right collarbone areas, and left and right armpits areas, and wherein said administering includes applying the product with the stable water clusters on the acupoints in associated with the hot spots in said areas.

\* \* \* \* \*